United States Patent [19]

Kuzma

[11] Patent Number: 4,516,820
[45] Date of Patent: May 14, 1985

[54] COCHLEAR PROSTHESIS PACKAGE CONNECTOR

[75] Inventor: Janusz Kuzma, Stanmore, Australia

[73] Assignee: The Commonwealth of Australia, Australia

[21] Appl. No.: 461,617

[22] Filed: Jan. 27, 1983

[51] Int. Cl.³ .............................................. H01R 25/00
[52] U.S. Cl. .................... 339/48; 339/49 B; 339/94 M; 339/60 M; 128/784
[58] Field of Search ................. 3/1, 1.1; 128/419, 784; 339/48, 49 B, 17 LM, 17 M, 92, 193, 194, 59 M, DIG. 3

[56] References Cited

U.S. PATENT DOCUMENTS

| | | | |
|---|---|---|---|
| 3,340,491 | 9/1967 | Deakin | 339/194 R |
| 3,419,844 | 12/1968 | Schmued | 339/48 |
| 3,441,897 | 4/1969 | Charlade | 339/48 |
| 3,573,710 | 4/1971 | Wofford | 339/49 B |
| 3,648,002 | 3/1972 | Du Rocher | 339/DIG. 3 |
| 3,701,964 | 10/1972 | Cronin | 339/17 M |
| 3,960,424 | 6/1976 | Weisenburger | 339/17 M |
| 3,994,552 | 11/1976 | Selvin | 339/49 B |
| 4,045,107 | 8/1977 | Southerland | 339/48 |
| 4,239,312 | 12/1980 | Myer et al. | 339/49 B |

Primary Examiner—Gil Weidenfeld
Assistant Examiner—David L. Pirlot
Attorney, Agent, or Firm—Gottlieb, Rackman & Reisman

[57] ABSTRACT

A cochlear prosthetic package having an electronics part and an electrode part. The two parts have ceramic plates with aligned, hermetically-sealed hollow-pin feedthroughs therein. The parts are connected by a Silastic sheet having individual metal foil pieces extending therethrough, each piece of metal foil having its two ends bent over to lie flush against respective faces of the Silastic sheet. The metal foil ends contact the feedthroughs to establish the electrical connections.

10 Claims, 6 Drawing Figures

COCHLEAR PROSTHESIS PACKAGE CONNECTOR

DESCRIPTION

This invention relates to implantable medical electronic devices such as pacemakers and cochlear prostheses, and more particularly to a cochlear prosthesis in which a plurality of connections are made between the assembly containing the electronic circuits, and an electrode or other conductor-type device.

In its usual form, a cochlear prosthesis consists of two parts implanted into the skull of the patient. The first part is an "electronics" package which is implanted in the mastoid bone behind the ear. The second part consists of an electrode assembly which is inserted into the cochlea in order to apply electrical stimulation to auditory nerve fibers. The electrode array or assembly must be electrically connected to the electronics package. In addition, an internally-worn transmitter/receiver device is used to transfer both information and power to the implanted unit, and may receive information telemetered back from the implant.

A major problem with a cochlear prosthesis is that entire replacement of the device is probably not feasible with present-day technology. The electrode assembly, once it has been implanted into the cochlea, probably cannot be explanted without damage to the cochlea itself. The electrode assembly must thus be designed to have a long life (in the order of fifty years, or the expected life of the patient). However, it may be necessary or desirable to replace the electronics package, for example, due to a circuit failure, or to substitute a compatible assembly of more advanced design at some time in the future. Thus, permanent connections between the electronics package and the electrodes are not appropriate.

In a cochlear prosthesis, the connection problem is much more severe than in the case of a pacemaker for several reasons. First, a pacemaker usually requires only a small number of connections to electrodes (up to four in existing designs), whereas 22 connections are required between the electronics package and the electrodes in a cochlear prosthesis such as that of the illustrative embodiment of the invention. Second, because of the confined space in the skull where the cochlear prosthesis is required to fit, the space constraints are much more severe than with a pacemaker. In addition, it is desirable for surgical convenience and safety to be able to make all connections between the electronics package and the electrodes simultaneously, with one procedure, which contrasts with a typical pacemaker design for which the small number of connections required allows each one to be made individually, for example, with grub screws.

Furthermore, as is the case with pacemakers and other implantable devices, the re-connection process must take place in an environment where fluid ingress cannot be prevented; since the electrode assembly remains permanently in the skull, each re-connection of the electrodes to a new electronics package must take place inside the patient's head.

It will be apparent to those skilled in the art that this type of connector problem is not confined to medical prostheses. In fact, there are a variety of situations in the electronics field where it is necessary to make a connection or connections to an electronics assembly in a hostile or difficult environment, such as in marine, petrochemical, industrial or automotive applications. The subject invention is applicable to fields other than medical prostheses.

Several cochlear prostheses have been described in the prior art, including some where a connector is provided. See, for example, reports under NIH Contract No. N01-NS-7-2367, "Development of Multichannel Electrodes for an Auditory Prosthesis". Connectors for use with implantable medical electronic devices have also been described. See, for example, U.S. patent application Ser. No. 237,090, entitled "Bone Growth Stimulator Connector", filed on Feb. 23, 1981 in the name of John B. Dickson. The prior art connector techniques, however, suffer from disadvantages which are solved by the subject invention.

The present invention relates to the design of a package for a cochlear prosthesis as described in my copending patent application entitled "Cochlear Prosthesis Package and Method for Making Same", Ser. No. 402,227, filed on July 27, 1982, which application is hereby incorporated by reference. The connection problem in my earlier design was solved by providing a two-part connector. One part consists of a ceramic plate or sheet containing a number of tubular platinum feedthroughs which form the electrical paths between the internal electronic circuits and the outside. These platinum feedthroughs are inserted into holes made in the ceramic while it is still in the green or unfired state. The platinum and ceramic are fired together and, as the ceramic sinters, it shrinks. The shrinking process exerts a force evenly around and along each platinum tubular feedthrough, with the result that an hermetic, high-strength reaction body is formed between the platinum and the ceramic. After firing, the surface of the ceramic plate is lapped to a mirror finish, and this assembly is then attached to the electronics assembly and a titanium housing using conventional soldering, welding and brazing techniques.

The second part of the connector consists of a Silastic sheet containing preformed platinum parts to which are welded wires connected to the electrodes. To this Silastic sheet is attached another Silastic sheet which acts as an insulating material, and due to its elasticity evenly distributes the force applied over the contact area. This force is applied by means of a titanium backing part, through the middle of which passes a screw attached to the other side of the connector.

Although this connector performs satisfactorily, it has been found to have some drawbacks. First, the elasticity of the connector is derived from the Silastic sheet in the connector part which is attached to the electrodes and thus remains inside the body. The long-term performance of this Silastic material is not fully known. Any deficiencies in the mechanical properties of the material which might be uncovered with the passage of time cannot be overcome without replacing the electrodes.

Second, the connector presents some difficulties in manufacture because of the difficulty of forming the small platinum preformed connector parts with a correctly shaped nail or conical head, with consistent shape and quality, and additionally because of the problem of welding the very fine platinum wires from the electrodes to the platinum parts.

It was also found that the process of tightening up the connector had the potential for stressing the very fine wires from the electrode array to the connector parts to such an extent that the welds might break or the wires fracture.

Finally, it is now thought that the small size of the head of each preformed platinum part might allow it to deform the Silastic sheet to such an extent that the platinum part could become so deeply embedded in the Silastic sheet that adequate pressure is not maintained, resulting in a loss of contact.

The present invention overcomes these limitations, and offers some other significant improvements and advantages to be described. It is an object of my invention to produce a connector suitable for use in implantable medical electronic devices, and in particular a cochlear prosthesis, and which is easily manufacturable; allows for reliable disconnection and re-connection without compromising the electrode array which is required to remain in the body; is not subject to degradation in mechanical performance over time; maintains both a high electrical resistance between different connected circuits, and a low-resistance, reliable contact between individual connector parts of the same electrical circuit; allows the opportunity to take advantage of new materials which may be developed in the future with more advantageous mechanical or electrical properties; is suitable for multiple, independent electrical connections in a small space; is designed such that the part of the connector which remains in the body attached to the electrodes has no elastic components which affect the performance of the connector or components which might suffer from degradation of properties with the passage of time; allows modularity of component selection such that one of a family of cochlear implant devices may be connected to one of a family of electrodes (e.g., of different size); and permits different types of electronic modules to be utilized with the same connector (e.g., an all ceramic package), and in particular allows advantage to be taken of new technology, materials, and manufacturing methods as they are developed.

Further objects, features and advantages of the invention will become apparent upon consideration of the following detailed description in conjunction with the drawing, in which.

Figure 1:
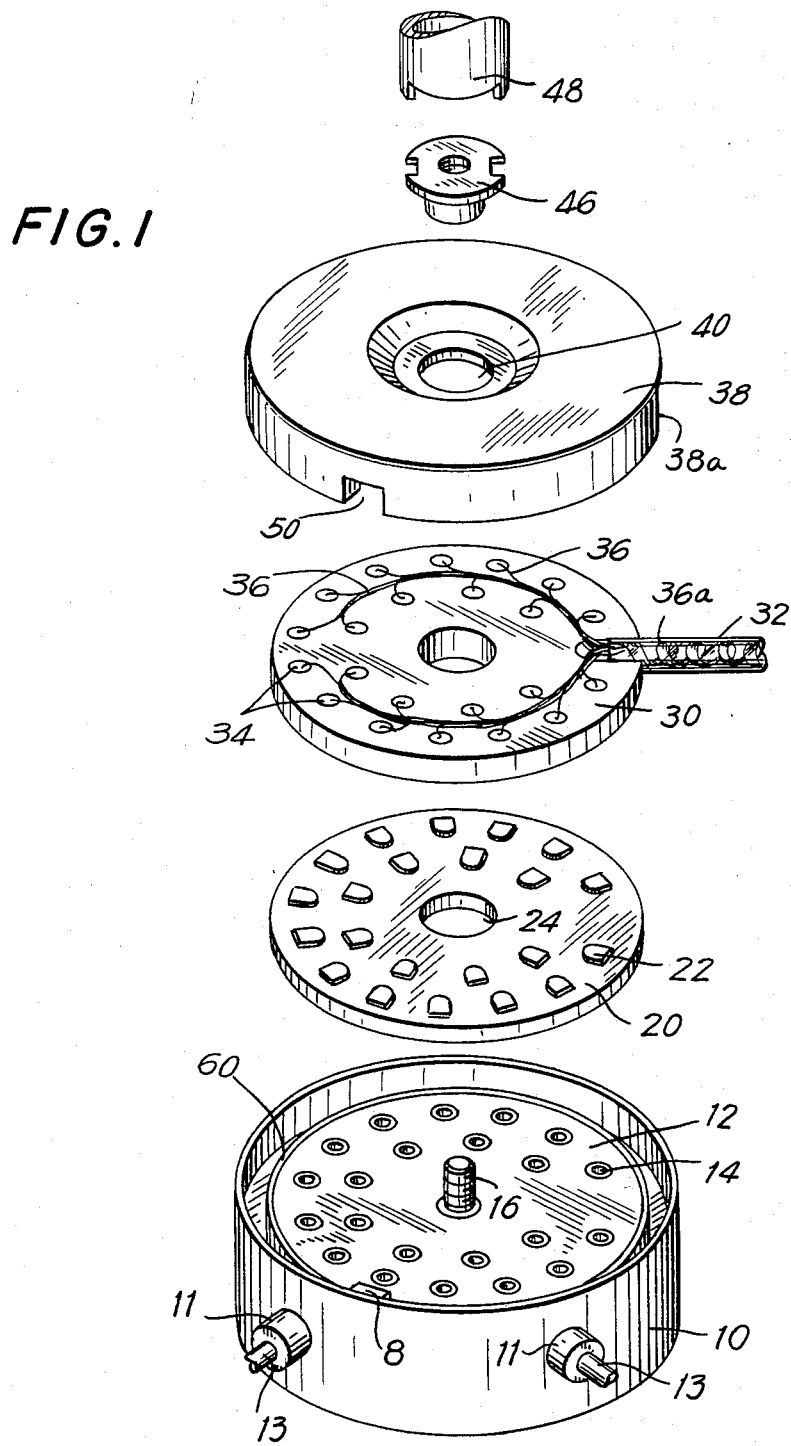
FIG. 1 is an exploded perspective view of the connector parts of a cochlear implant package made in accordance with the principles of my invention.

Referring to FIG. 1, one side of the connector arrangement consists of a cochlear implant device such as that described in my copending application. In fact, one of the advantages of the present invention is that one side of the connector need not be changed. The electronics assembly is contained in a titanium housing or case 10, to which is attached, by welding and brazing in the conventional way, a plate (preferably ceramic) 12 containing hermetic platinum feedthroughs 14, as previously described above. A titanium screw 16 projects from the center of the ceramic plate. The surface of the ceramic plate is lapped to a mirror finish. The titanium housing contains hermetic feedthroughs 11 to a two-ended tube 13 (shown only partially), through which a coil (not shown) passes, as described in my copending application.

Figure 2:
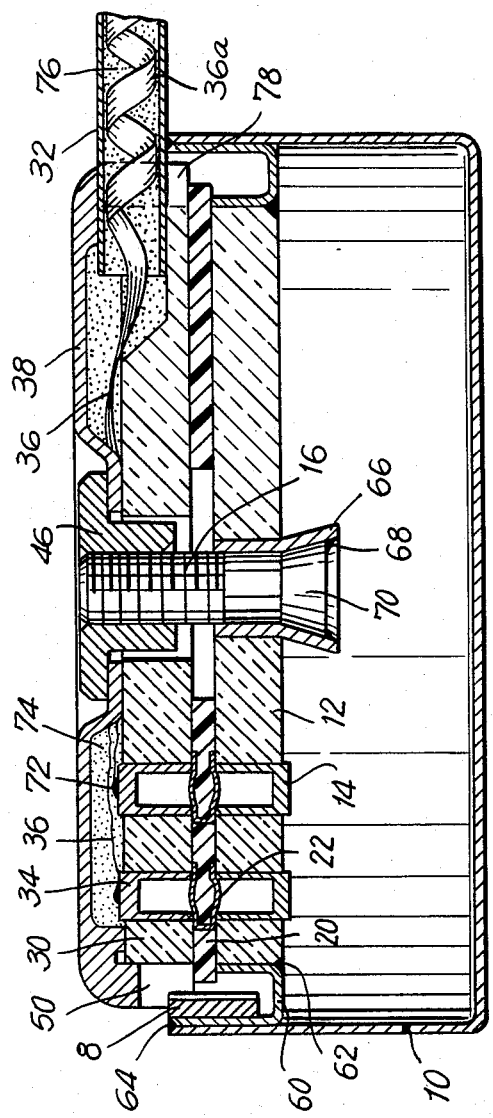
FIG. 2 is a detailed cross-sectional view of the connector parts showing them assembled together.

The other side of the connector consists of a plate (preferably ceramic) 30 with identical feedthroughs 34, shown end on in FIG. 1 and illustrated in cross-section in FIG. 2. Ceramic plate 30 is made of identical components and with an identical process as the ceramic plate 12 containing the feedthroughs which is used in the electronics package. Some minor machining operations are used to convert the ceramic plate with feedthroughs which is used in the electronics package for use in the electrode side of the connector.

As shown in FIG. 1, ceramic plate 30 is backed by a titanium plate 38. A titanium piece 8 is accurately welded to the inside of the circumference of the titanium housing 10 to act as a locating pin or lug. This locating lug fits into a depression 50 machined into the titanium backing piece 38 to ensure that the connector is assembled while correctly aligned.

The titanium locating lug 8 is shown in one position in FIG. 1, and in a different position in FIG. 2. The exact position of the locating lug is not critical. In fact, the locating lug can be looked upon not only as a locating lug but also a keying system. That is to say, future generations of cochlear implants and/or electronic packages may use a different number of locating lugs in different positions such that it is not possible to mix elements from imcompatible families. For example, the connector technique described herein could be used to make a connector with, for example, 50 connection points in the same area, and a different locating and keying arrangement could be used to prevent mix-up of incompatible components.

In the center of the titanium backing piece 38 is a hole 40 through which the screw 16 attached to the other part projects. The assembly is completed by a titanium nut 46 screwed onto screw 16. A predetermined torque is applied to the screw via a special tool 48 used with any conventional torque spanner (not shown). A slot or cutout 38a is machined in the titanium backing piece to allow exit of the cable to be described below.

In the illustrative embodiment of the invention, the force holding the connector together is applied by the centrally located screw and nut. Other arrangements centrally located (e.g., a clip, or a screw passing entirely through the package) are also suitable. Alternatively, or in addition, the force could be applied by a collar, ring or band outside the connector, where in this case there would not be a need for a central hole in the connector.

The electrode leads 36 are formed into a spiral 36a inside a Silastic tube 32 as it exits the connector. The tube is also filled with Silastic (MDX 4-4210). The purpose of the spiralling is to provide stress relief of the electrode cable so that fracture due to fatigue resulting from flexing is prevented. The Silastic is transparent, allowing visual inspection of the cable after manufacture.

Between the two ceramic plates containing feedthroughs there is disposed a thin Silastic sheet 20. Into this Silastic sheet are placed small pieces of platinum foil 22, each passing from one side of the sheet, through a small respective cut or slit, to the other side. A central hole 24 in the Silastic sheet allows passage of the screw 16. Thus, connection between paired feed-throughs is made via a platinum foil piece pressed against and between the Silastic sheet and the platinum feed-throughs in the ceramic plates on both sides of the connector. In the preferred embodiment, the interconnecting Silastic sheet is glued in a couple of spots to the ceramic plate with platinum feedthroughs in the electronics package, with the correct alignment being established visually at the time of gluing; in this manner, the sheet can be held in place during assembly. However, a larger Silastic sheet could be used with cut-outs for alignment with the locating lug 8.

After assembly of the complete cochlear prosthesis, the entire implantable device is surrounded by a silicon rubber (Silastic 4515, Type A) protective coating or shield (not shown). The purpose of this shield is to act as a protective coating for the implant to prevent tissue growth into cavities and corners in the implant which might make removal of the implant more difficult, to protect the body from sharp edges or corners on the implant and to protect the implant during handling such as during surgical implantation and electrode insertion.

The performance of the device is not dependent upon the integrity of the shield as the electronics package is hermetically sealed. Nor is the performance of the connector dependent upon fluids being excluded by the shield, as it is designed to perform even if connection is made totally immersed in saline, or other physiological fluids.

Referring to FIG. 2 which shows the connector arrangement in cross-sectional detail, it can be seen that the electronics component of the implant is constructed as described in my copending application. A ceramic sheet or plate 12 contains platinum feedthroughs 14. The plate is attached to a machined or pressed titanium flange 60 by a high-temperature brazing process using a braze 62 capable of hermetically joining ceramic and titanium. The flange and ceramic assembly with feedthroughs have the electronic components attached (not shown), and the entire assembly is TIG-welded using conventional techniques, shown by the numeral 64, to the titanium bottom part 10 of the appropriate dimensions.

In the center of the ceramic plate 12 is attached a titanium screw 16 using one of several methods. As illustrated, a platinum tube 66 is bonded to the ceramic plate at the same time as the feedthroughs. The titanium screw 16 is then embedded firmly into the platinum tube, and hermeticity is ensured by braze 68 between the platinum tube and the titanium screw. The head 70 of the screw is appropriately shaped for location, sealing, and force transfer, as will be apparent to those skilled in the art.

Ceramic plate 30 with platinum feedthroughs 34 is used on the other side of the connector. Instead of a central platinum tube, the central hole is enlarged to accommodate an extension of the tightening nut 46.

In fact, an advantage of the subject connector design is that the ceramic plate on the electrode side of the connector is almost identical to the ceramic plate on the electronics package side; the two are made with the same components and processes. Defects in components or manufacturing processes will produce a number of ceramic assemblies with platinum tube feedthroughs which are not hermetic, and therefore unsuitable for use in the electronics package. However, these components are perfectly suitable for use on the electrode side of the connector since feedthrough hermeticity is not a requirement on this side. Thus, provided the reject rate of the platinum-to-ceramic sintering process remains below 50%, all parts manufactured may be used. It is anticipated, however, that advances in technology and materials may result in different materials being used for the connector plates, where both sides are not the same. My invention is also useful in applications where it is necessary to join two hermetically sealed parts with electrical connections; in such a case, both sides of the connector would need to be made from hermetic assemblies.

The ceramic plate 30 on the electrode side of the connector has the fine wires 36 from the electrodes welded to the platinum feedthroughs 34, as shown by the numeral 72. These wires are mechanically supported after welding by Silastic glue (Type A), shown by the numeral 74. All 22 electrode wires exit as a bundle 36a which is wound in a spiral supported in Silastic tube 32 embedded with Silastic 76. The purpose of the spiraling of the electrode wire bundle is to act as a strain relief and prevent electrode wire fracture due to fatigue as a result of flexing, stetching or other movement while in the body, during insertion, or during manufacture or transport. The electrode cable exits the connector via a cutout 78 in the titanium backing plate 38.

The titanium backing plate 38 is shaped so that it makes contact with the ceramic plate 30 at the periphery and circumferentially, and also in the center where the nut 46 is located. There is a thin film 74 of Silastic between the titanium backing plate 38 and the ceramic plate 30. Thus, as the titanium nut is tightened, force is transmitted from the nut, through the titanium backing plate, via the thin film of Silastic to the ceramic connector plate. The hole in the center of the ceramic plate fits snugly around the nut and centrally locates the connector around the screw. This arrangement of tightening ensures that forces transmitted to the electrode side of the connector are evenly distributed over the entire surfaces of the ceramic plates.

The other function of the titanium backing plate 38 is to protect the delicate electrode wires embedded in the soft Silastic as they pass from the electrode bundle 36a to where they are welded to the connector feedthroughs. The backing plate in the preferred embodiment is titanium, but other materials are suitable as long as the forces holding the connector together with a central screw are transmitted via a metal part against the ceramic feed-through plate.

Because the cavity between the titanium backing plate and the ceramic plate with feedthroughs to which the electrode wires are attached is filled with Silastic 74, additional support for the electrode wires is provided. Thus, the entire electrode side of the connector is solid and contains no parts or components which may be subject to fatigue or creep failure over the expected life of the electrodes, or will be otherwise adversely affected by the passage of time.

Figure 3:
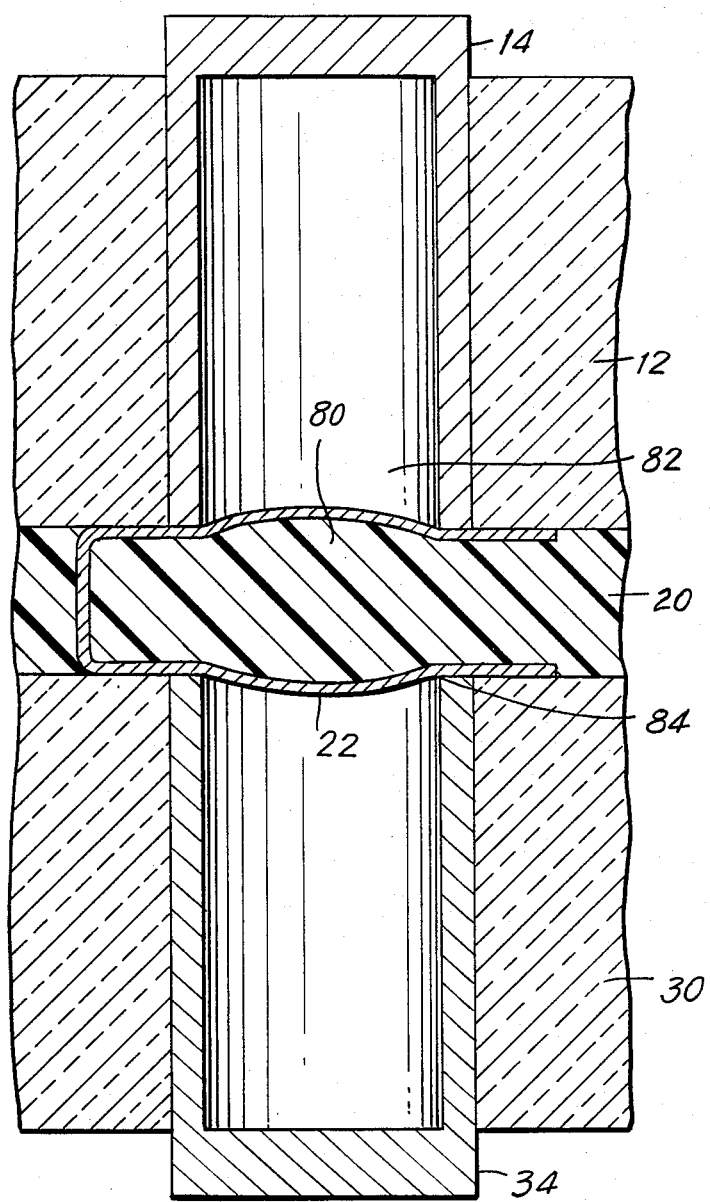
FIG. 3 is an enlarged view of a single connection point.

Between the two ceramic plates 12 and 30 there is disposed Silastic sheet 30, containing a number of platinum foil parts 22 inserted through slits cut into the Silastic sheet and then bent over. An enlarged view of the Silastic sheet in the region of the platinum feedthrough parts is shown in FIG. 3. The thickness of the platinum foil and the Silastic sheet should be accurately controlled. I have found that 25-micron thick platinum foil and a 500-micron thick Silastic sheet give satisfactory results.

The platinum foil 22 makes contact in the form of a ring with each feedthrough platinum part. Since there is a thickness of the Silastic sheet, and twice the thickness of the platinum foil between each pair of platinum connector feedthroughs, the Silastic sheet in the region of contact is more deformed than elsewhere; thus, the force pressing the platinum foil onto the platinum feedthroughs can be accurately controlled. Even if there is a misalignment of parts such that the platinum feedthroughs are not coaxial, there will always be a region where two thicknesses of platinum foil, and one thickness of Silastic, lie between feedthrough platinum tubes (provided, of course, that the axes of the tubes do not stray more than one diameter from each other).

However, since the platinum feedthroughs are preferably hollow (for reasons explained in my copending application), there is only little force tending to deform the Silastic sheet in the center of the feedthroughs, and thus the Silastic tends to bulge in this region, as shown by the numeral 80. The space 82 in the middle of each platinum feedthrough is important. The purpose of this hole or space is to allow plastic deformation of the Silastic sheet into the hole, and there is thus a transition zone between Silastic under high pressure outside the area of the hole, and Silastic under no pressure. Therefore, there is always a region of Silastic between the two extremes where the elastic limit is not exceeded and, even if the Silastic sheet deforms plastically due to creep, the platinum foil will be pressed against the platinum feedthroughs with a fairly constant force by the Silastic still within the elastic limit. In addition, the inside edge 84 of the hole in each platinum feedthrough is fairly sharp, so the contact pressure is high. Since platinum is a fairly ductile material, the foil tends not to be cut by these forces, but deforms to make an excellent contact around the entire circumference of each platinum feedthrough.

The Silastic and platinum interconnecting part is designed to be replaced at each re-connection. Thus, if there is any creep of the Silastic material during the expected life of the implant, a new Silastic sheet may be inserted when re-connection is performed. In addition, this design has the option to take advantage of new materials which may be developed or become available in future years without modifying the intrinsic design or nature of the connector, as discussed above.

In the preferred embodiment, the interconnecting Silastic sheet containing the platinum foil pieces is supplied attached by glue (Silastic, Type A) in a couple of spots to the electronics package, but it is possible to supply it separately.

Referring to FIG. 2, the entire assembly is located by a small titanium lug 8 which is resistance welded to the electronics package after TIG-welding of the titanium sections together. This locating lug is designed to fit inside a complementary shaped slot 50 machined into the titanium backing piece 38. The geometrical arrangement of the components, with particular regard to the locating lug and the electrode exit point, is designed to ensure that correct alignment is maintained during assembly.

Figure 4A:
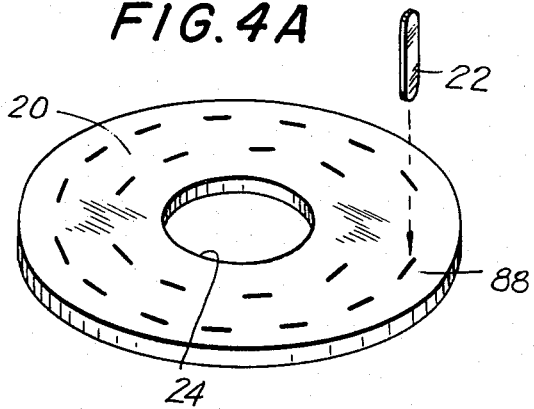
FIGS. 4A-4C illustrate the steps of the preferred method of manufacturing the intervening Silastic sheet containing the platinum contacts.
Figure 4B:
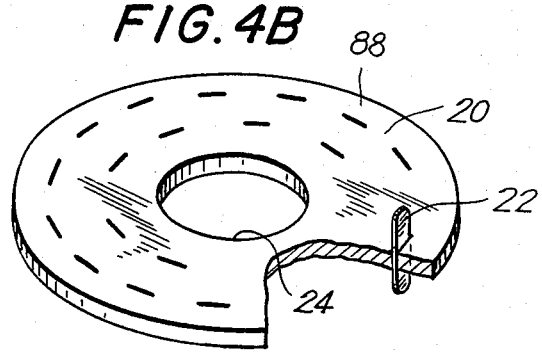
Figure 4C:
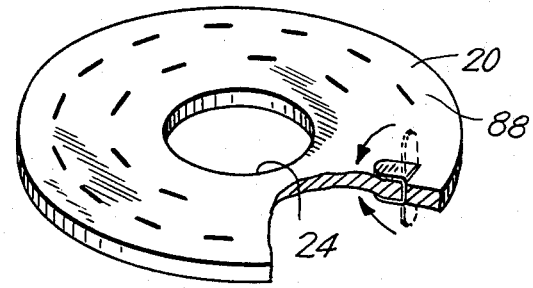

FIGS. 4A-4C illustrate diagrammatically the method of construction of the Silastic interconnection sheet with the platinum foil parts. In the upper part of the figure, a Silastic sheet 30 is depicted; the sheet is molded from the appropriate Silastic (Type 4210) between two sheets of optically flat glass separated by a precisely known distance. A central hole 24 to allow passage of the screw is punched or cut in the Silastic sheet. Additionally, 22 slits shown by the numeral 88, are punched or cut in the sheet to one side of the positions where the feedthrough platinum pieces are to be inserted. Preformed platinum (or other noble metal) foil pieces 22 are punched or cut from a platinum foil sheet of a known and controlled thickness. These pieces are inserted into the slits in the Silastic sheet, as shown in the middle part of the figure, so that equal amounts protrude from either side of the Silastic sheet. Each foil piece is then folded over as shown in the lower part of the figure, to form the interconnection. The foil pieces are shown in the drawing to be of approximately rectangular shape with rounded ends, but other shapes (e.g., kidney or figure eight) are possible.

It is important that the surfaces of the two ceramic plates be lapped to a mirror finish. A high electrical resistance between adjacent contacts is assured because no path for conductive fluid exists between adjacent connections except in the spaces between each ceramic plate and the Silastic sheet. With smooth surfaces on the ceramic plates and the Silastic sheet, and a known and controlled tightening torque, high interconnection resistances are routinely observed, even when the connection is made entirely under saline. The process of tightening the connector tends to force out any fluid which may have been inside the connector prior to tightening.

Disconnection of the connector is made by cutting around the perimeter of the protective Silastic shield (not shown) with a blade and removing the Silastic shield over the electrode side of the connector. The nut is then unscrewed, and the connector opened. The electronics package with interconnecting sheet can then be removed.

During replacement of the electronics package, the connection is made and the nut is tightened so that the correct torque is applied. Then a pre-molded Silastic covering part may be attached over the electrode side of the connector, and attached to the Silastic covering over the electronics assembly with Silastic Medical Grade adhesive, Type A.

Although the invention had been described with reference to a particular embodimenet, it is to be understood that this embodiment is merely illustrative of the application of the principles of the invention. Numerous modifications may be made therein and other arrangements may be devised without departing from the spirit and scope of the invention.

I claim:

1. A connector arrangement for connecting to each other first and second parts of a cochlear prosthesis, said first part having an hermetically sealed case adapted to contain an electronic circuit therein and said second part having a plurality of conductors extending therefrom; each of said first and second parts having a carrier with a plurality of noble-metal conducting hollow-tube feedthroughs extended therethrough and hermetically sealed thereto by reaction bonds; the two pluralities of feedthroughs having alignable patterns; a deformable sheet permanently adhered to the carrier of said first part and having a plurality of noble-metal foil contacts extending through respective slits each having its two ends bent over so that they lie flush against respective faces of said sheet, said plurality of contacts having a pattern which is alignable with the patterns of the feedthroughs in said two pluralities; each of said feedthroughs being open at that end which faces said deformable sheet and the face of each of said carriers which is disposed adjacent to said deformable sheet being lapped to a mirror finish; a screw extending outwardly of the carrier of said first part and passing through a central hole in the carrier of said second part for securing said sheet between said first and second parts to allow said plurality of contacts to establish electrical connections between respective ones of the feedthroughs in said two pluralities; said second part including a backing plate having a central hole therein, and said securing means further including a nut screwable onto the end of said screw which extends through said backing plate hole; and a plurality of conductors connected to respective ones of the feedthroughs in said second part, said plurality of conductors being wound in the form of a spiral and exiting said second part through an additional hole in said backing plate.

2. A connector arrangement in accordance with claim 1 wherein the carriers of said first and second parts are substantially identical.

3. A connector arrangement in accordance with claim 2 further including Silastic material surrounding the conductors in said second part between the carrier and backing plate thereof.

4. A connector arrangement in accordance with claim 3 further including mating means on said first and second parts for ensuring the proper alignment thereof.

5. A connector arrangement for connecting to each other first and second parts of a cochlear prosthesis, said first part having an hermetically sealed case adapted to contain an electronic circuit therein and said second part having a plurality of conductors extending therefrom; said first part having a carrier with a plurality of conducting means extended therethrough and hermetically sealed thereto; characterized by said second part having a carrier with a plurality of conducting means extended therethrough, the two pluralities of conducting means having alignable patterns; a deformable sheet having a plurality of contacts each having one end on each respective face of said sheet, said plurality of contacts having a pattern which is alignable with the patterns of the conducting means in said two pluralities; a screw extending outwardly of the carrier of said first part and passing through a central hole in the carrier of said second part for securing said sheet between said first and second parts to allow said plurality of contacts to establish electrical connections between respective ones of said conducting means in said two pluralities; said second part including a backing plate having a central hole therein, and securing means further including a nut screwable onto the end of said screw which extends through said backing plate hole; and a plurality of conductors connected to respective ones of the conducting means in said second part, said plurality of conductors being wound in the form of a spiral and exiting said second part through an additional hole in said backing plate.

6. A connector arrangement in accordance with claim 5 further including Silastic material surrounding the conductors in said second part between the carrier and backing plate thereof.

7. A connector arrangement for connecting to each other a first part having an hermetically sealed case adapted to contain an electronic circuit therein and a second part having a plurality of conductors extending therefrom; said first part having a carrier with a set of hollow-tube feedthroughs hermetically-sealed thereto by reaction bonds; said second part having a carrier with a set of hollow-tube feedthroughs, the two sets of feedthroughs having alignable patterns; a deformable sheet having a set of contacts each having one end on each respective face of said sheet, said set of contacts having a pattern which is alignable with the patterns of the feedhtroughs in said two sets and each of said feedthroughs being open at that end which faces said deformable sheet; a screw extending outwardly of the carrier of said first part and passing through a central hole in the carrier of second second part for securing said sheet between said first and second parts to allow said set of contacts to establish electrical connections between respective ones of the feedthroughs in said two sets; said second part including a backing plate having a central hole therein, and securing means further including a nut screwable onto the end of said screw which extends through said backing plate hole; and a set of conductors connected to respective ones of the feedthroughs in said second part, said set of conductors being wound in the form of a spiral and exiting said second part through an additional hole in said backing plate.

8. A connector arrangement in accordance with claim 7 further including Silastic material surrounding the conductors in said second part between the carrier and backing plate thereof.

9. A connector arrangement for connecting to each other a first part having an hermetically sealed case adapted to contain an electronic circuit therein and a second part having a plurality of conductors extending therefrom; said first part having a carrier with a set of hermetically-sealed, hollow-tube feedthroughs; characterized by said second part having a carrier with a set of hollow-tube feedthroughs; the two sets of feedthroughs having alignable patterns; a deformable sheet having a set of contracts each having one end on each respective face of said sheet, said set of contacts having a pattern which is alignable with the patterns of the feedthroughs in said two sets; a screw extending outwardly of the carrier of said first part and passing through a central hole in the carrier of said second part for securing said sheet between said first and second parts to allow said set of contacts to establish electrical connections between respective ones of said feedthroughs in said two sets; a backing plate in said second part having a central hole therein; a nut screwable onto the end of said screw which extends through said backing plate hole; and a set of conductors connected to respective ones of the feedthroughs in said second part, said set of conductors being wound in the form of a spiral and exiting said second part through an additional hole in said backing plate.

10. A connector arrangement in accordance with claim 9 further including Silastic material surrounding the conductor in said second part between the carrier and backing plate thereof.

* * * * *